US00PP30431P3

(12) United States Plant Patent
Ranney

(10) Patent No.: US PP30,431 P3
(45) Date of Patent: Apr. 23, 2019

(54) ***HYDRANGEA* PLANT NAMED 'NCHA8'**

(50) Latin Name: *Hydrangea arborescens*
Varietal Denomination: NCHA8

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/731,345

(22) Filed: May 30, 2017

(65) Prior Publication Data

US 2018/0352698 P1 Dec. 6, 2018

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

*Primary Examiner* — Keith O. Robinson
(74) *Attorney, Agent, or Firm* — Cassandra Bright

(57) ABSTRACT

A new and distinct *Hydrangea* cultivar named 'NCHA8' is disclosed, characterized by large, mop-head inflorescences with florets that open green and progress to white. Plants have a compact, rounded and upright habit with strong stems. Plants are triploid. The new variety is a *Hydrangea* normally produced as an outdoor garden or container plant.

3 Drawing Sheets

Latin name of the genus and species: *Hydrangea arborescens*.
Variety denomination: 'NCHA8'.

BACKGROUND OF THE INVENTION

The present invention comprises a new and distinct *hydrangea* cultivar hereinafter referred to by the cultivar name 'NCHA8'. This new *hydrangea* was developed through a breeding program at North Carolina State University, Mills River, N.C. 'NCHA8' was selected from a population of seedlings that resulted from a cross of *Hydrangea arborescens* 'H2009-068-007' (unpatented pollen parent) and *Hydrangea arborescens* 'H2008-143-001' (unpatented seed parent). See FIG. 1 for a complete pedigree. The first asexual propagation of 'NCHA8' was carried out in July 2012 by rooting stem cuttings at the North Carolina State University, Mountain Horticultural Crops Research Station, Mills River, N.C. and has been asexually reproduced repeatedly by vegetative cuttings over a two year period. 'NCHA8' roots readily from softwood cuttings treated with a basal dip of 2,500-5,000 ppm indole butyric acid (potassium salt) in water. 'NCHA8' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Large mop-head inflorescences with florets that open green and progress to white.
2. Triploid cytotype.
3. Upright, rounded habit with strong stems.

COMPARISON WITH COMMERCIAL CULTIVARS

Table 1 shows distinguishing characteristics between 'NCHA8' and commercially available cultivars of *H. arborescens*. 'NCHA8' has a unique combination of traits including flowers with green-white sepals, a compact growth habit, and triploid cytotype.

TABLE 1

Comparison to commercial cultivars.

| | Taxa | | |
|---|---|---|---|
| Trait | *H. arborescens* 'NCHA1' (U.S. Plant Pat. (No. 20,765) | *H. arborescens* 'NCHA5' (15/731,346) | *H. arborescens* 'NCHA7' (15/731,344) |
| Ploidy level (genome size, pg) | Diploid (2.7) | Triploid (3.9) | Triploid (3.9) |
| Growth habit | Rounded | Rounded, dwarf | Rounded |
| Height and width | 100 cm × 100 cm | 35 cm × 55 cm | 80 cm × 80 cm |
| Stem internode length | 5 to 15 cm | Avg. 7 cm (4 to 10.5 cm) | Avg. 6 cm (4 to 7 cm) |
| Flower count | | | |
| Fertile | Approx. 600 | Approx. 450 | Approx. 50 |
| Sterile | Approx. 600 | Approx. 900 | Approx. 200 |
| Corymb diameter | 8-20 cm | Avg. 16 cm | Avg. 14 cm |
| Sepal color | | | |
| Above | Red-Purple (ranges from 68D/C to N66D/N66C) | White (155A) to White (N155D) | Red-Purple (60C) |

TABLE 1-continued

| Comparison to commercial cultivars. | | | |
|---|---|---|---|
| Below | Red-Purple (ranges from 68D/C to N66D/N66C) | White (155A) to White (N155D) | Red-Purple (60A) |
| Sepal | | | |
| Length | 0.5-0.7 cm | Avg. 0.5 cm | Avg. 0.8 cm |
| Width | 0.3-0.5 cm | Avg. 0.4 cm | Avg. 0.8 cm |

| | Taxa | |
|---|---|---|
| Trait | *H. arborescens* 'NCHA8' | *H. arborescens* 'PIIHA-I' (U.S. Plant (Pat. No. 21,227) |
| Ploidy level (genome size, pg) | Triploid (3.9) | Unknown |
| Growth habit | Rounded | Upright, spreading |
| Height and width | 60 cm × 60 cm | 90 cm × 90 cm |
| Stem internode length | Avg. 7 cm (3 to 10 cm) | About 6 cm |
| Flower count | | |
| Fertile | Approx. 500 | Approx. 75 |
| Sterile | Approx. 300 | Approx. 300 |
| Corymb diameter | Avg. 14 cm | Avg. 12.5 cm |
| Sepal color | | |
| Above | Yellow-Green (145C) fading to Green-White (157C) | Close to Red-Purple (58A) |
| Below | Yellow-Green (145D) | Close to Red-Purple (63A) |
| Sepal | | |
| Length | Avg. 0.5 cm | 0.7 cm |
| Width | Avg. 0.3 cm | 0.5 cm |

COMPARISON WITH PARENT VARIETIES

The new variety is similar to the parent varieties in most horticultural aspects. The new variety differs from the seed parent in the following:

1. Sterile sepals of 'NCHA8' are colored a white to green in color, compared to the light red-purple sterile sepals of the seed parent.

The new variety is similar to the parent varieties in most horticultural aspects. The new variety differs from the pollen parent in the following:

1. Sterile sepals of 'NCHA8' are colored a white to green in color, compared to the light red-purple sterile sepals of the pollen parent.
2. Plants of 'NCHA8' produce more sterile florets (about 500) per inflorescence than the pollen parent (about 165).

BRIEF DESCRIPTION OF THE DRAWINGS

This new *hydrangea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *hydrangea*.

DETAILED BOTANICAL DESCRIPTION

Figure 1:
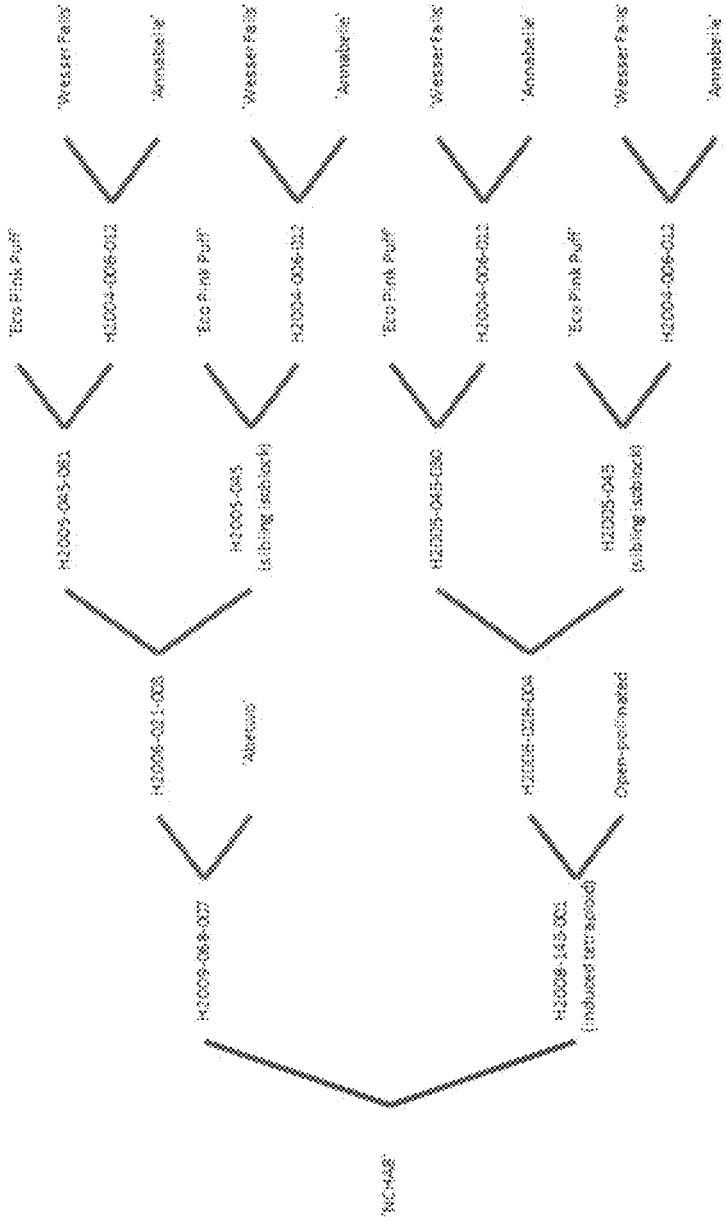
FIG. 1 Shows the pedigree of 'NCHA8'.
Figure 2:
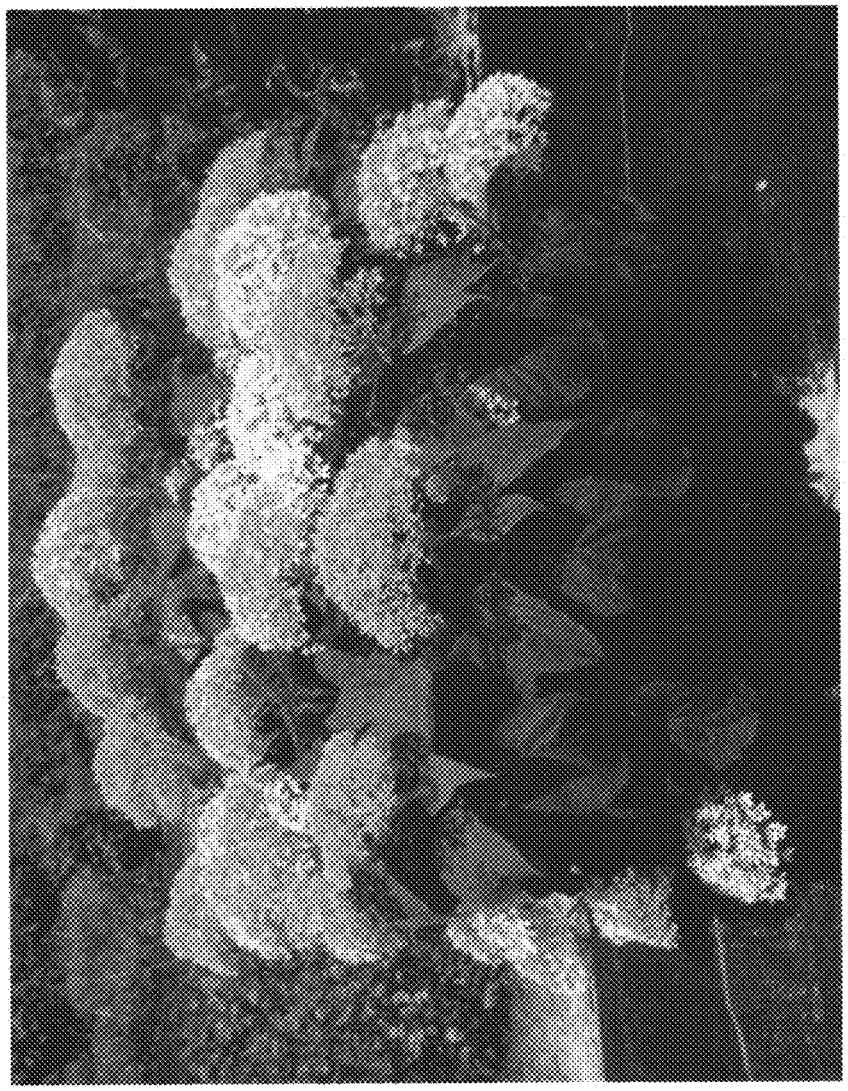
FIG. 2 Shows the inflorescence and plant form of a two-year-old plant of 'NCHA8'.
Figure 3:
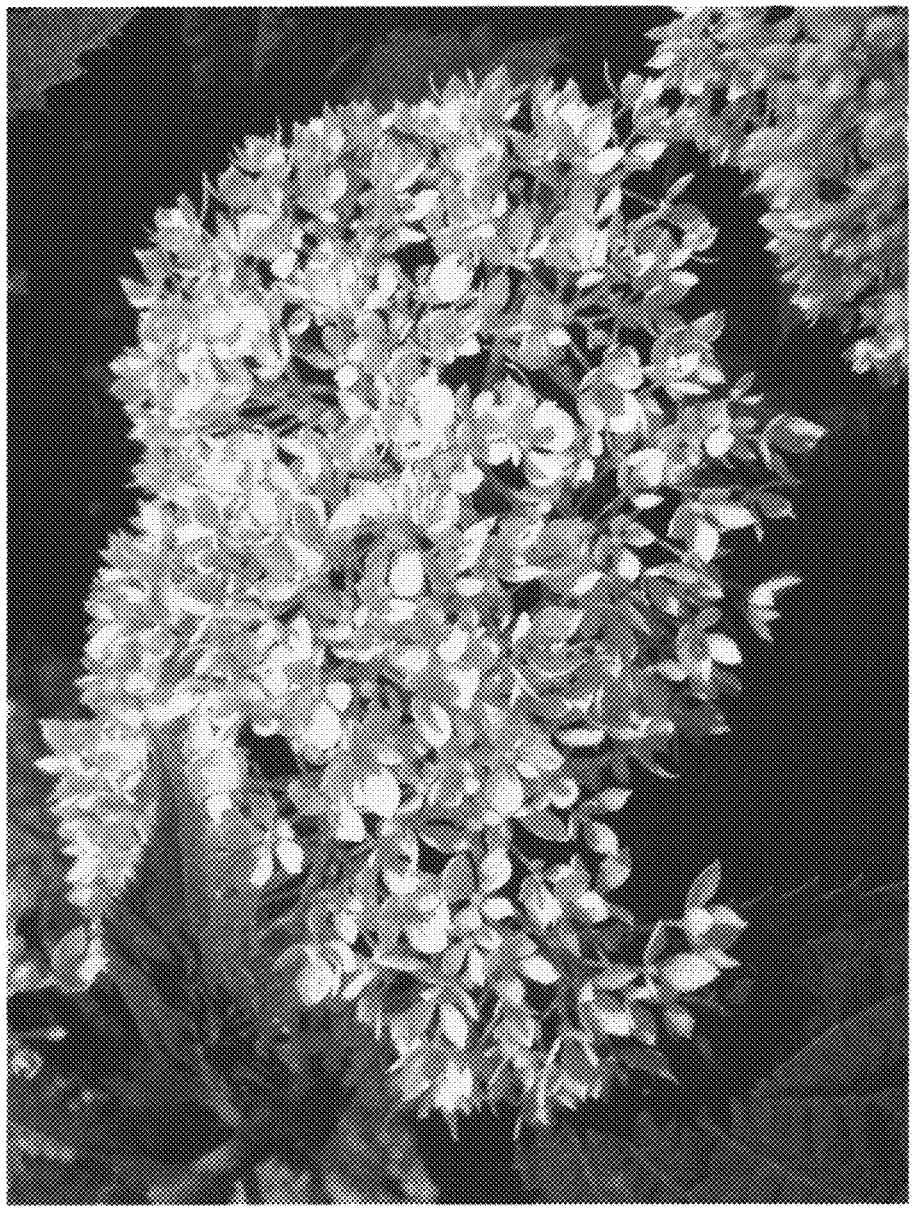
FIG. 3 Shows the inflorescence of a two-year-old plant of 'NCHA8'.

The following is a detailed description of the botanical characteristics of the new and distinct *hydrangea* variety plant known by the denomination 'NCHA8'. The detailed description was taken on a two-year-old field-grown plant in Mills River, N.C. in 2016. All colors cited herein refer to The Royal Horticultural Society Colour Chart (The Royal Horticultural Society (R.H.S.), London, Sixth Edition, 2015). Where specific dimensions, sizes, colors, and other characteristics are given, it is to be understood that such characteristics are approximations or averages set forth as accurately as practicable.

Classification:

*Botanical name.*—*Hydrangea arborescens* 'NCHA8'.

*Common name.*—Smooth *Hydrangea.*

Parentage: 'NCHA8' originated as a seedling that resulted from a cross of *H. arborescens* 'H2009-068-007' and *H. arborescens* 'H2008-143-001'.

Plant:

*Growth habit.*—Rounded. Non-climbing.

*Height* (*from top of soil including inflorescences*).—About 60 cm.

*Width* (*including inflorescences*).—About 60 cm.

Shoot and stem:

*Length.*—60 cm (20 to 60 cm).

*Diameter.*—0.5 cm (0.3 to 0.9 cm).

*Internode length.*—7 cm (3 to 10 cm).

*Immature shoot texture* (*current year*).—Pubescent.

*Immature shoot color* (*current year*).—Yellow-Green (146C).

*Mature stem texture* (*from prior year*).—Glabrous, exfoliating.

*Mature stem color* (*from prior year*).—Grey-Brown (199D).

*Fasciation.*—Absent.

*Lenticels.*—Absent.

Branching habit: Freely branching with 40-60 shoots.

Foliage:

*Type.*—Simple.

*Persistence.*—Deciduous.

*Arrangement.*—Opposite.

*Shape.*—Broadly ovate.

*Lobing.*—Absent.

*Apex.*—Acuminate.

*Base.*—Acute to rounded.

*Venation.*—Pinnate, opposite to subopposite.

*Vein color.*—Upper: Yellow-Green (148B). Lower: Yellow-Green (148D).

*Margins.*—Dentate to serrate.

*Texture.*—Upper surface: Slightly pubescent. Lower surface: Slightly pubescent.

*Emerging leaves.*—Color: Upper and lower: Yellow-Green (146A).

*Mature leaves during growing season.*—Color: Upper: Green (137A). Lower: Yellow-Green (146A). Length of lamina: Avg. 7.5 cm (4.5 to 9.0 cm). Width: Avg. 5 cm (3 to 7 cm).

*Leaf attachment.*—Petiolate.

*Petiole.*—Length: Avg. 1.5 cm (0.5 to 2.5 cm). Diameter: Avg. 0.2 cm (0.1 to 0.2 cm). Color: Green (148B).

Inflorescence:

*Description.*—Fertile (approximately 300) and sterile (approximately 500) flowers arranged on individual globular, hemispherical or dome-shaped terminal, compound corymbs.

*Flowering season.*—Late May to late June in Mills River, N.C.

*Corymb.*—Diameter: Average 14 cm (10 to 15 cm). Height: Average 8 cm (5 to 10 cm). Quantity: Often 50-80 corymbs per plant over the flowering season. Longevity: Showy for approximately 4 weeks.

*Sterile flowers.*—Petals, pistils and stamens are greatly reduced (<0.5 mm). Inconspicuous. Buds: Shape: Oval. Diameter: 0.2 cm. Color: Yellow-Green (145A). Sepals: Number: 2 to 5. Length: Avg. 0.5 cm (0.3 to 0.7 cm). Width: Avg. 0.3 cm (0.2 to 0.5 cm). Shape: Ovate. Apex: Mucronate to rounded. Base: Rounded. Margin: Entire. Texture: Glabrous. Color: Upper: Yellow-Green (145C) fading to Green-White (157C). Lower: Yellow-Green (145D).

*Fertile flowers.*—Sepals and petals are greatly reduced (<0.5 mm). Buds: Shape: Round. Diameter: 0.2 cm. Color: Yellow-Green (145B). Width: 0.2 cm. Height: 0.2 cm.

Reproductive organs:

*Gynoecium.*—Pistil number: 2, fused. Pistil color: Green-White (157B). Pistil length: 0.1 cm. Stigma shape: Blunt. Stigma diameter: 0.05 cm. Style length: 0.1 cm. Ovary shape: Rounded. Ovary diameter: 0.05 cm.

*Androecium.*—Stamen number: 10. Anther: Shape: Rounded, fusiform. Length: 0.05 cm. Color: Yellow-Green (145C). Filament: Length: 0.07 cm. Color: Yellow-Green (145C). Amount of pollen: None observed.

Other characteristics:

Fruit/seed set: Seeds are minute, dust-like.

Disease and insect resistance: No significant resistance nor susceptibility to disease or insect pests have been observed.

Cold hardiness: At least USDA zone 6b; testing has not been completed in colder zones.

What is claimed is:

1. A new and distinct cultivar of *Hydrangea arborescens* plant named 'NCHA8' as illustrated and described herein.

* * * * *